(12) United States Patent
Alam et al.

(10) Patent No.: US 10,330,596 B1
(45) Date of Patent: Jun. 25, 2019

(54) APPARATUS AND METHOD FOR TESTING THE ABILITY OF MATERIALS TO PROTECT PHOTOLABILE MATERIALS

(71) Applicant: KING SAUD UNIVERSITY, Riyadh (SA)

(72) Inventors: Mohd Aftab Alam, Riyadh (SA); Fahad Ibrahim Al-Jenoobi, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 15/937,464

(22) Filed: Mar. 27, 2018

(51) Int. Cl.
*G01N 21/59* (2006.01)

(52) U.S. Cl.
CPC .................... *G01N 21/59* (2013.01)

(58) Field of Classification Search
CPC ........................................ G01N 21/59
USPC ................... 356/432–444, 244–246
See application file for complete search history.

(56) References Cited

U.S. PATENT DOCUMENTS

| | | | | |
|---|---|---|---|---|
| 4,310,249 A | * | 1/1982 | Kramer | G01N 21/255 250/228 |
| 4,762,798 A | * | 8/1988 | Deutsch | G01N 21/75 356/246 |
| 5,644,239 A | | 7/1997 | Huang et al. | |
| 6,680,777 B1 | | 1/2004 | Wollert et al. | |
| 2016/0033783 A1 | * | 2/2016 | Maeda | G02B 27/283 356/218 |

FOREIGN PATENT DOCUMENTS

| FR | 2453405 A1 | 10/1980 |
|---|---|---|
| GB | 20143000 A | 8/1979 |
| GB | 2402207 A | 12/2004 |

OTHER PUBLICATIONS

Cyanuric Acid Test Kit, LaMotte Company website, Copyright 2017, 2 pages.

* cited by examiner

*Primary Examiner* — Tri T Ton
(74) *Attorney, Agent, or Firm* — Richard C. Litman

(57) ABSTRACT

The apparatus and method for testing the ability of materials to protect photolabile materials provides an accurate measurement by directly observing the degradation level in a photolabile material. The apparatus is an assembly having primary and secondary cells and a light source. The primary and secondary cells are arranged in different configurations with respect to one another such that any light that reaches the photolabile materials must first go through the protective material under test. The method includes placing a protective material under test in the primary cell; placing a photolabile material in the secondary cell; subjecting the assembly to a light source for a predetermined amount of time; and removing and testing the photolabile material for degradation.

19 Claims, 13 Drawing Sheets

APPARATUS AND METHOD FOR TESTING THE ABILITY OF MATERIALS TO PROTECT PHOTOLABILE MATERIALS

BACKGROUND

1. Field

The disclosure of the present patent application relates to laboratory testing apparatus, and particularly to an apparatus and method for testing the ability of materials to protect photolabile materials against light induced/triggered degradation.

2. Description of the Related Art

Photolabile or photosensitive materials are materials that degrade in the presence of light. The extent of photodegradation or photodecomposition is different for different materials. The photodecomposition of a photolabile substance may lead to changes in physicochemical properties, or to decreased potency and efficacy of medicinal or pharmaceutical products. Some medicinal or pharmaceutical products may show significant loss in potency in a short span of time, while others may maintain their potency and only undergo physicochemical changes, for example, a change in color. It is therefore important to provide a photolabile substance/material in a composition with at least one suitable protective material, which can protect the photolabile substance/material against photodegradation. Further, the photolabile substance can also be placed in packaging including a protective material. Previous methods for testing such protective materials involve intimately mixing the photolabile substance/material and the protective material. When screening a large number of materials for their protective ability, there is a fair chance that some of the materials under test can significantly interfere in the analysis of the photolabile substance, when present in same composition. Further, there is a chance of physicochemical and or chemical interaction if the protective material under test is intermixed with the photolabile substance. In such situations, it is difficult to obtain reliable data.

Thus, an apparatus and method for testing the ability of materials to protect photolabile materials solving the aforementioned problems is desired.

SUMMARY

The apparatus and method for testing the ability of materials to protect photolabile materials provides an accurate measurement by directly observing the degradation level in a photolabile material. The apparatus is an assembly having primary and secondary cells and a light source. The primary and secondary cells are arranged in different configurations with respect to one another such that the protective material under test in the primary cell comes in the way of light generated by the light source before the light reaches the photolabile materials in the secondary cell, such that any light that reaches the photolabile materials must first go through the protective material under test. The configurations include one or more secondary cells within a primary cell, or parallel cells with one or more common transparent separating walls. The method includes placing a protective material under test in the primary cell; placing a photolabile material in the secondary cell; subjecting the assembly to a light source for a predetermined amount of time; and removing and testing the photolabile material for degradation. The light source can be selected from sunlight, a laboratory light or a light source as suggested in guidelines for photostability testing of new drug substances and products. The apparatus and method for testing the ability of materials to protect photolabile materials keeps the photolabile material and the protective material under test separated, so there is no chance of any direct interaction between the photolabile material and the protective material under test. Thus, the samples of photolabile substances can be analyzed by using single analytical method, as there is no interference of the protective material on the analysis of the photolabile substance.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
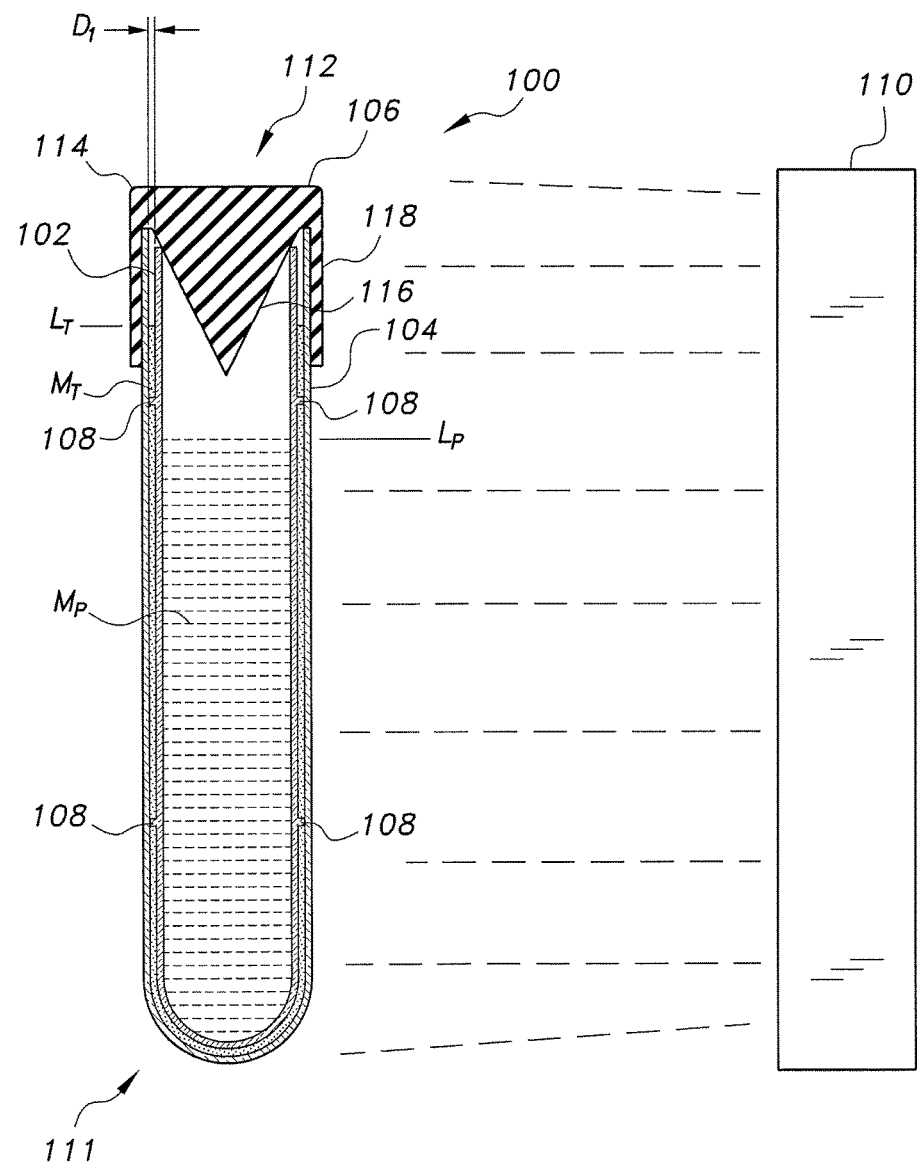
FIG. 1 is a front view of a first embodiment of an apparatus for testing the ability of materials to protect photolabile materials.

The apparatus for testing the ability of materials to protect photolabile materials has several different embodiments. As shown in FIG. 1, a first embodiment of the apparatus 100 includes a primary transparent cell 104 and a secondary transparent cell 102. In this embodiment, the secondary transparent cell 102 fits within the primary transparent cell 104. The primary transparent cell 104 and secondary transparent cell 102 are cylindrical tubes closed at one end 111 and open at the other end 112, similar to test tubes. The secondary transparent cell 102 includes six small peg-like projections 108 on the outer surface of the side wall of the secondary transparent cell 102. These projections 108 are arranged at two different levels, and keep the secondary transparent cell 102 centrally aligned within the primary transparent cell 104. The projections 108 also maintain an equal gap $D_1$ on all sides between the inner wall of primary transparent cell 104 and the outer wall of the secondary transparent cell 102, defining an annular test chamber. The material under test $M_T$ is placed in the annular test chamber, in the gap between the inner wall of primary transparent cell 104 and the outer wall of the secondary transparent cell 102. The photolabile material $M_P$ is placed inside the secondary transparent cell 102. The level $L_P$ of photolabile material $M_P$ inside the secondary transparent cell 102 is maintained lower than the level $L_T$ of the material under test $M_T$, to avoid direct exposure of light on the photolabile material $M_P$. The thickness of the walls of the primary transparent cell 104 and the secondary transparent cell 102 is between 0.3 to 2 mm, more preferably 0.4 to 1.5 mm, and most preferably 0.5 to 1 mm. The internal diameter of the primary transparent cell 104 is between 3 to 15 mm, more preferably 4 to 10 mm, and most preferably 8 to 10 mm. The internal diameter of the secondary transparent cell 102 is between 1 to 5 mm, more preferably 1 to 4 mm, and most preferably 2 to 3 mm. The gap D1 between the transparent walls of primary cell 104 and secondary cell 102 is between 1 to 5 mm, more preferably 1 to 4 mm, and most preferably 1 to 3 mm from all sides.

The open end 112 of cells 102 and 104 is closed, using a closing cap 106. The cap 106 includes a body 114, a central projection 116 and peripheral wall 118. The central projection 116 fits inside the opening of secondary transparent cell 102, while the peripheral wall 118 of the cap 106 covers the outer wall of the primary transparent cell 104 near the open end 112 of the assembly. The level $L_T$ of the material under test $M_T$ is maintained above the lower end of the peripheral wall 118 of the cap 106 to avoid direct exposure of light onto the photolabile material $M_P$. Once the materials have been placed in the cells, the assembly is illuminated using a light source 110. The light source 110 can be placed at the top of the assembly 100 or to the side of the assembly 100. The photolabile material $M_P$ is withdrawn intermittently at predetermined time intervals and is analyzed to determine if any degradation of the photolabile material $M_P$ has occurred. The mixing or stirring of photolabile material $M_P$ inside the secondary cell 102 is not required. However, it may be mixed or stirred occasionally before sampling by using suitable stirring means (not shown).

Figure 2:
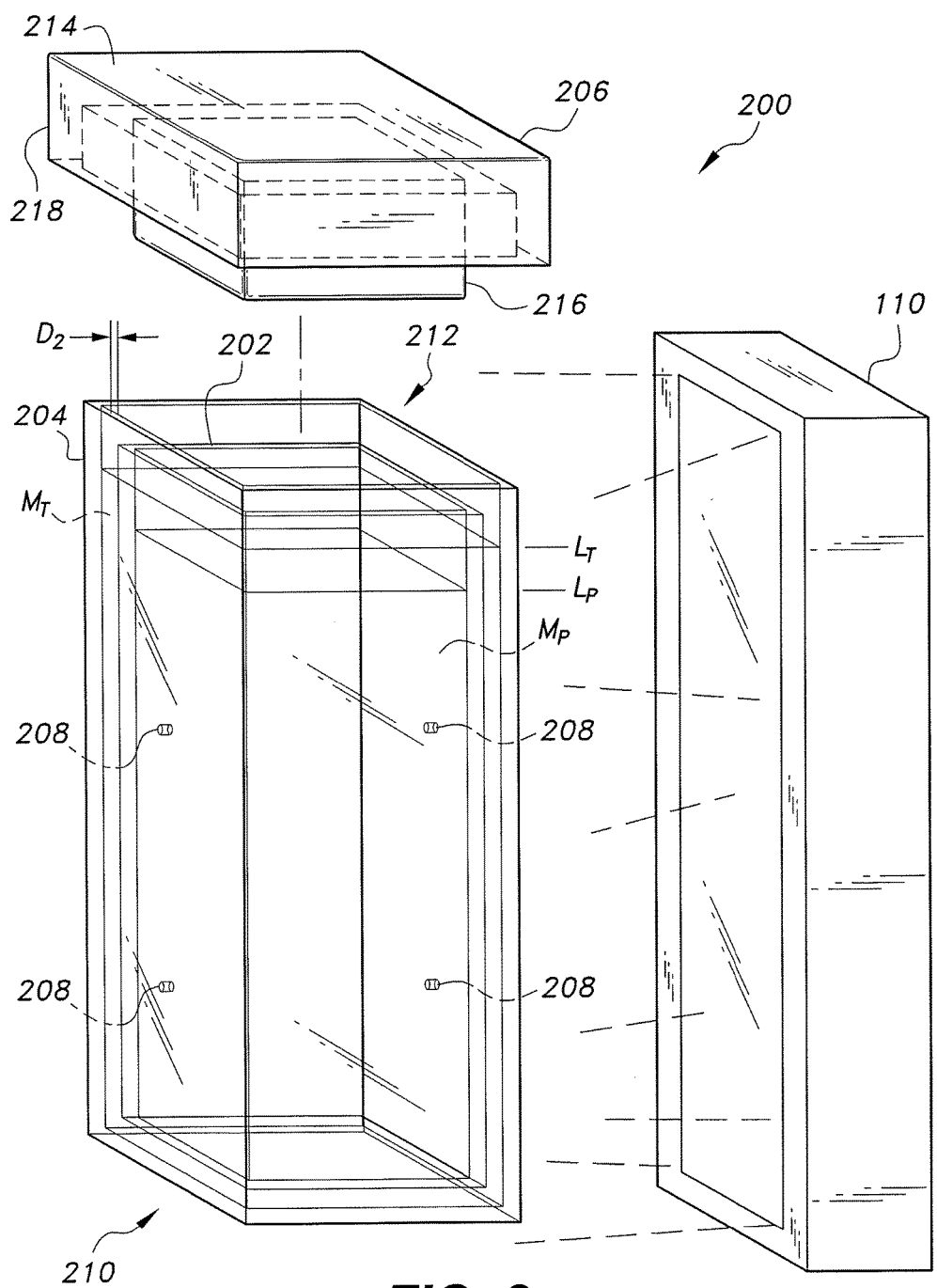
FIG. 2 is an environmental, perspective view of a second embodiment of an apparatus for testing the ability of materials to protect photolabile materials.

As shown in FIG. 2, a second embodiment of the apparatus 200 includes a primary transparent cell 204 and a secondary transparent cell 202. In this embodiment, as with the previous embodiment, the secondary transparent cell 202 fits within the primary transparent cell 204. The primary transparent cell 204 and secondary transparent cell 202 are cuvette-like structures closed at one end 210 and open at the other end 212, having a planar, substantially square bottom and four planar, substantially rectangular side walls that are orthogonal to the bottom and to each other. In one embodiment, all side walls of the primary transparent cell 204 and the secondary transparent cell 202 are transparent. The secondary transparent cell 202 includes peg like projections 208 on the outer surface of the side wall of the secondary transparent cell 202. The projections 208 keep the secondary transparent cell 202 centrally aligned and prevent shifting of the secondary transparent cell 202 within the primary transparent cell 204, as well as maintaining an equal gap $D_2$ between all side walls of primary transparent cell 204 and the side walls of the secondary transparent cell 202, defining a test chamber. The material under test $M_T$ is placed in the test chamber, in the gap between the inner wall of the primary transparent cell 204 and the outer wall of the secondary transparent cell 202. The photolabile material $M_P$ is placed inside the secondary transparent cell 202. The level $L_P$ of photolabile material $M_P$ inside the secondary transparent cell 202 is maintained lower than the level $L_T$ of the material under test $M_T$ to avoid direct exposure of light on the photolabile material $M_P$. The open end 212 of cells 202 and 204 is closed, using a closing cap 206. The cap 206 includes a body 214, a central projection 216 and peripheral walls 218. The central projection 216 fits inside the opening of the secondary transparent cell 202, while the peripheral walls 218 of the cap 206 cover the outer wall of the primary transparent cell 204 near the open end 212 of the assembly. Once the materials have been placed in the cells, the assembly is illuminated using the light source 110. The light source 110 can be placed at the top of the assembly 200 or to the side of the assembly 200. The photolabile material $M_P$ is withdrawn intermittently at predetermined time intervals and is analyzed to determine if any degradation of the photolabile material $M_P$ has occurred.

As noted above, in one embodiment, all four side walls of primary transparent cell 204 and secondary transparent cell 202 are transparent to allow for the transmission of light therethrough. In a further embodiment of the apparatus 200, two opposite side walls of the primary cell 204 and the secondary cell 202 are transparent, while the other two opposite side walls of the primary cell 204 and the secondary cell 202 are opaque to block the transmission of light therethrough.

Figure 3:
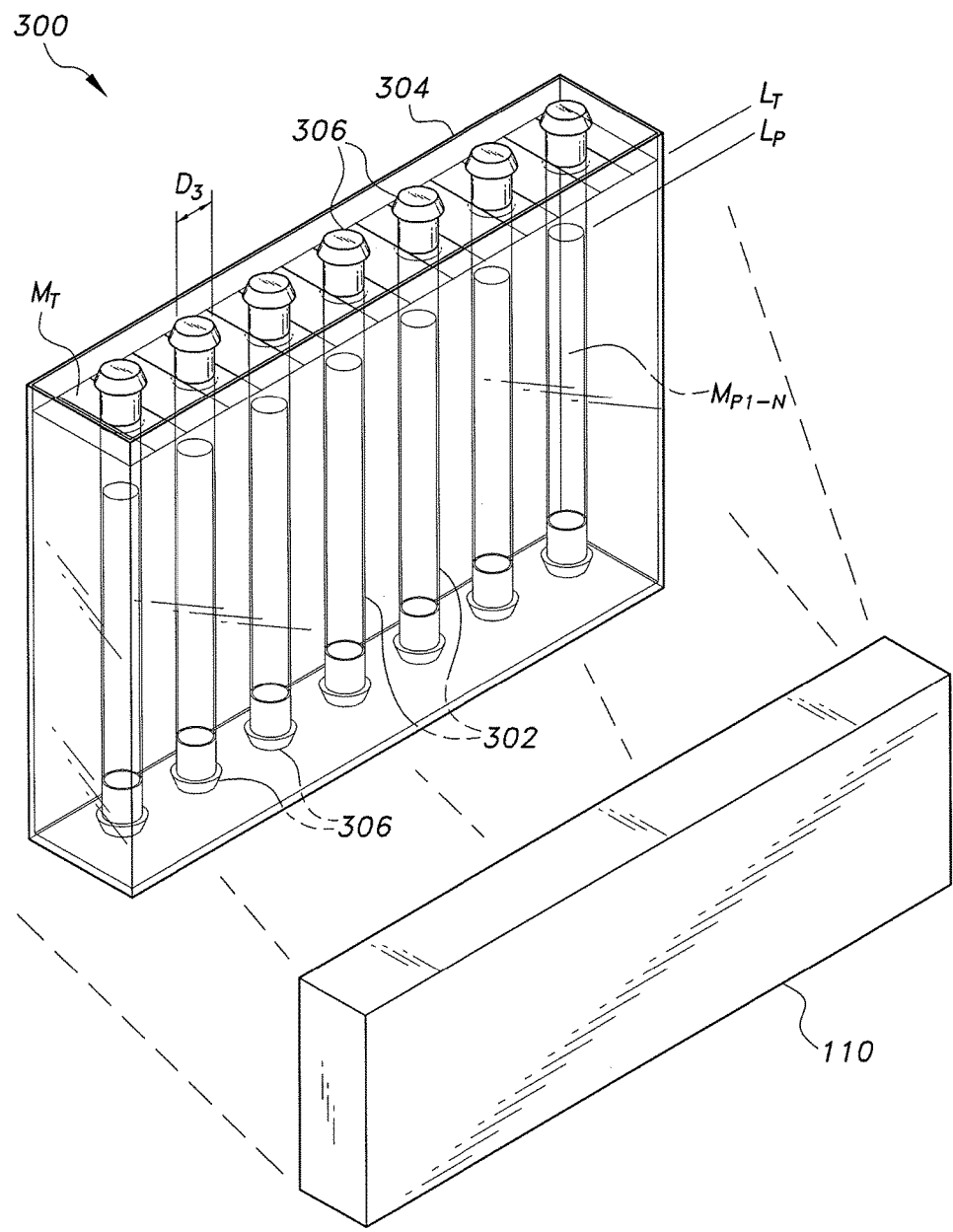
FIG. 3 is an environmental, perspective view of a third embodiment of an apparatus for testing the ability of materials to protect photolabile materials.
Figure 4:
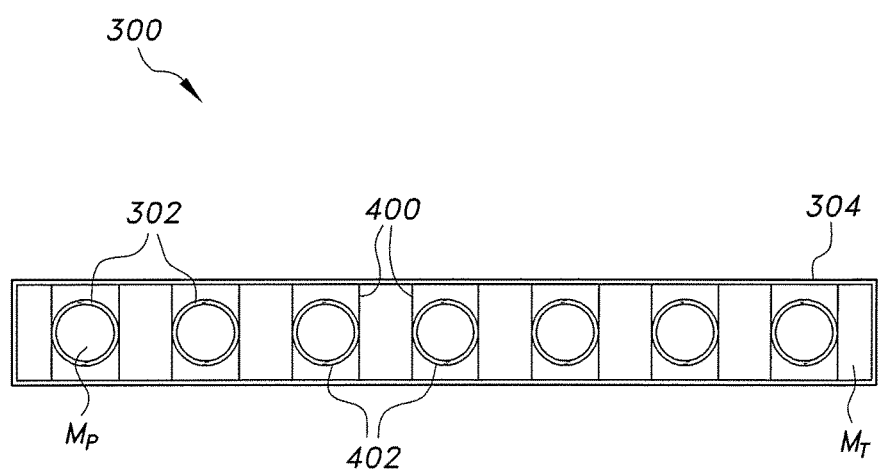
FIG. 4 is a top view of the apparatus of FIG. 3.

As shown in FIGS. 3-4, a third embodiment of the apparatus 300 includes a transparent primary cell 304 having a transparent, planar, substantially rectangular bottom and four planar, substantially rectangular side walls that are orthogonal to the bottom and to each other. The apparatus 300 also includes a plurality of transparent secondary cells 302 within the primary cell 304. The multiple transparent secondary cells 302 are transparent cylindrical capillaries or rectangular pipes with open ends. Alternatively, the multiple transparent secondary cells 302 may be in the form of pipes with rectangular cross sections. The wall thickness of the secondary cells 302 is between 0.3 to 3.0 mm, and preferably between 0.5 to 2.0 mm. The internal diameter $D_3$ of the secondary cells 302 is between 0.5 to 2.0 mm, and preferably between 0.5 to 1.0 mm. The photolabile material $M_{P1-N}$ is placed inside the secondary transparent cells 302. Both open ends of secondary cells 302 are closed using closing plugs 306. The material under test $M_T$ is placed in the transparent primary cell 304. As is shown in FIG. 4, a cell holder 400 is located at the top of the primary cell 304. The cell holder 400 includes a plurality of straight thin wires 400 and a plurality of small circular rings 402 of thin wire. The small circular rings 402 each surround a secondary cell 302, while the straight thin wires 400 extend between the rings 402 and the inner side walls of the transparent primary cell 304, thereby keeping the secondary cells 302 in an upright and spaced position within the transparent primary cell 304.

The level $L_P$ of photolabile material $M_{P1-N}$ inside the secondary transparent cells 302 is maintained lower than the level $L_T$ of the material under test $M_T$, to avoid direct exposure of light onto the photolabile material $M_{P1-N}$. All four side walls of the primary cell 304 are transparent. Once the materials have been placed in the cells, the assembly is illuminated using the light source 110. The light source 110 can be placed at the top of the assembly 300 or to the side of the assembly 300. The photolabile materials $M_{P1-N}$ are withdrawn intermittently at predetermined time intervals and are analyzed to determine if any degradation of the photolabile material $M_P$ has occurred. The different secondary cells 302 of the assembly 300 may comprise the same photolabile material or a number N of different photolabile materials, to allow testing for N different photolabile materials simultaneously.

Figure 5:
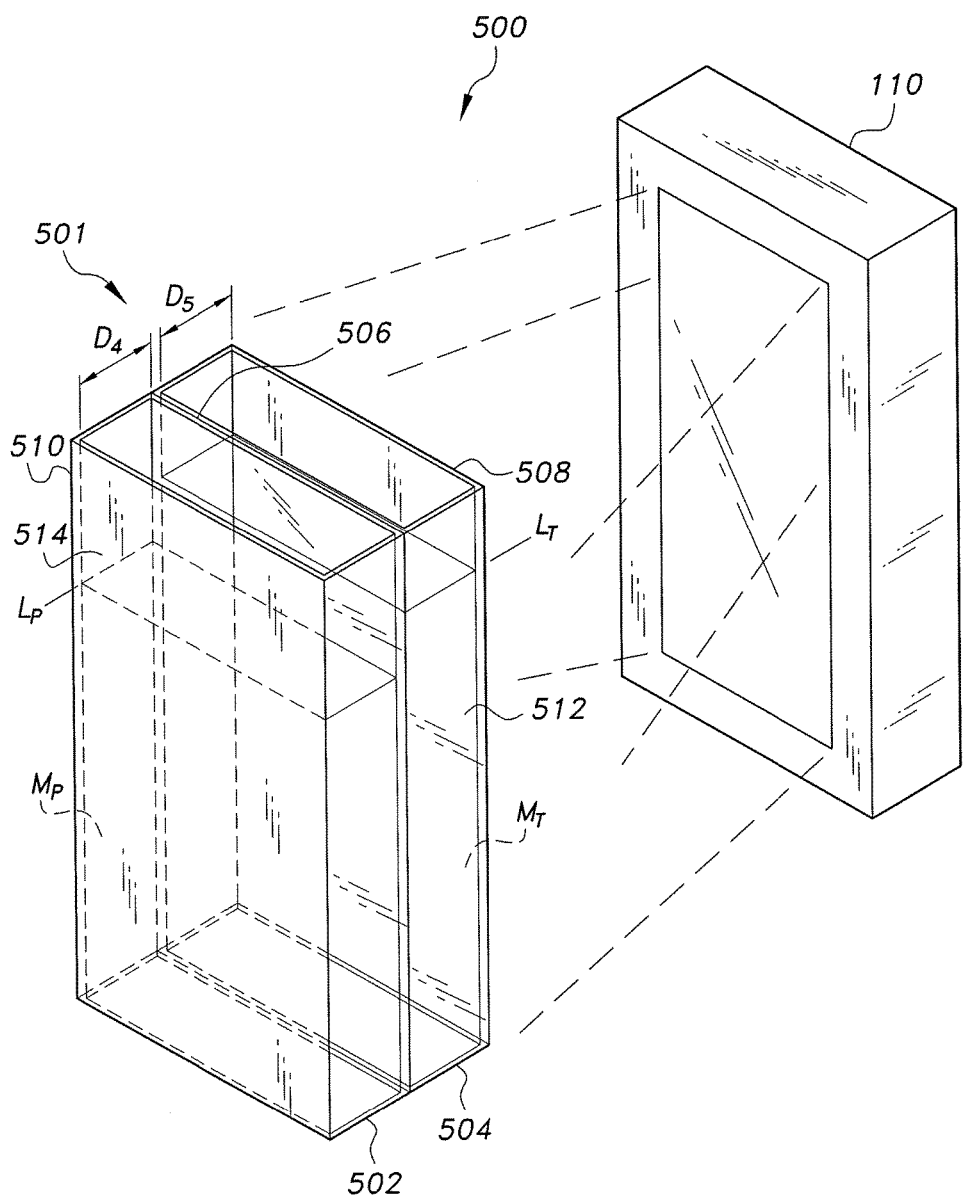
FIG. 5 is an environmental, perspective view of a fourth embodiment of an apparatus for testing the ability of materials to protect photolabile materials.

As shown in FIG. 5, a fourth embodiment of the apparatus 500 includes a unitary assembly 501, which has a primary cell 504 and a secondary cell 502 separated by a transparent separating wall 506. The separating wall 506 forms a common wall between the primary cell 504 and the secondary cell 502. The side wall 508 of primary cell 504 that is opposite to the separating wall 506 is transparent and allows the transmission of light into the primary cell 504. The bottom, the rear wall 510 and the front wall 512 of the unitary assembly 501, are opaque to block the transmission of light directly into the secondary cell 502, as well as to block the transmission of light into the secondary cell 502 through a shortened path through the primary cell 504. The side wall 514 of secondary cell 502 that is opposite to the separating wall 506 is opaque to block the transmission of light directly into the secondary cell 502. The photolabile material $M_P$ is placed inside the secondary cell 502. The material under test $M_T$ is placed in the primary cell 504. The level $L_P$ of photolabile material $M_P$ inside the secondary cell 502 is maintained lower than the level $L_T$ of the material under test $M_T$, to avoid direct exposure of light onto the photolabile material $M_P$. After filling the primary cell 504 and secondary cell 502, the open top of both the cells is closed with a suitable opaque closure (not shown). Once the materials have been placed in the cells, the assembly is illuminated using the light source 110. The light source 110 can be placed at the top of the assembly 500 or to the side of the assembly 500. The photolabile material $M_P$ is withdrawn intermittently at predetermined time intervals and is analyzed to determine if any degradation of the photolabile material $M_P$ has occurred.

The bottom, the side walls and the separating wall are all planar and substantially rectangular, and are all orthogonal to each other. The distance $D_4$ between the separating wall 506 and the opaque side wall 514 is preferably between 1.0 to 10.0 mm, more preferably between 1.0 to 6.0 mm, and most preferably 2.0 to 3.0 mm. The distance $D_5$ between the separating wall 506 and the transparent side wall 508 is between 1.0 to 10.0 mm, more preferably 1.0 to 6.0 mm, and most preferably 2.0 to 3.0 mm.

Figure 6:
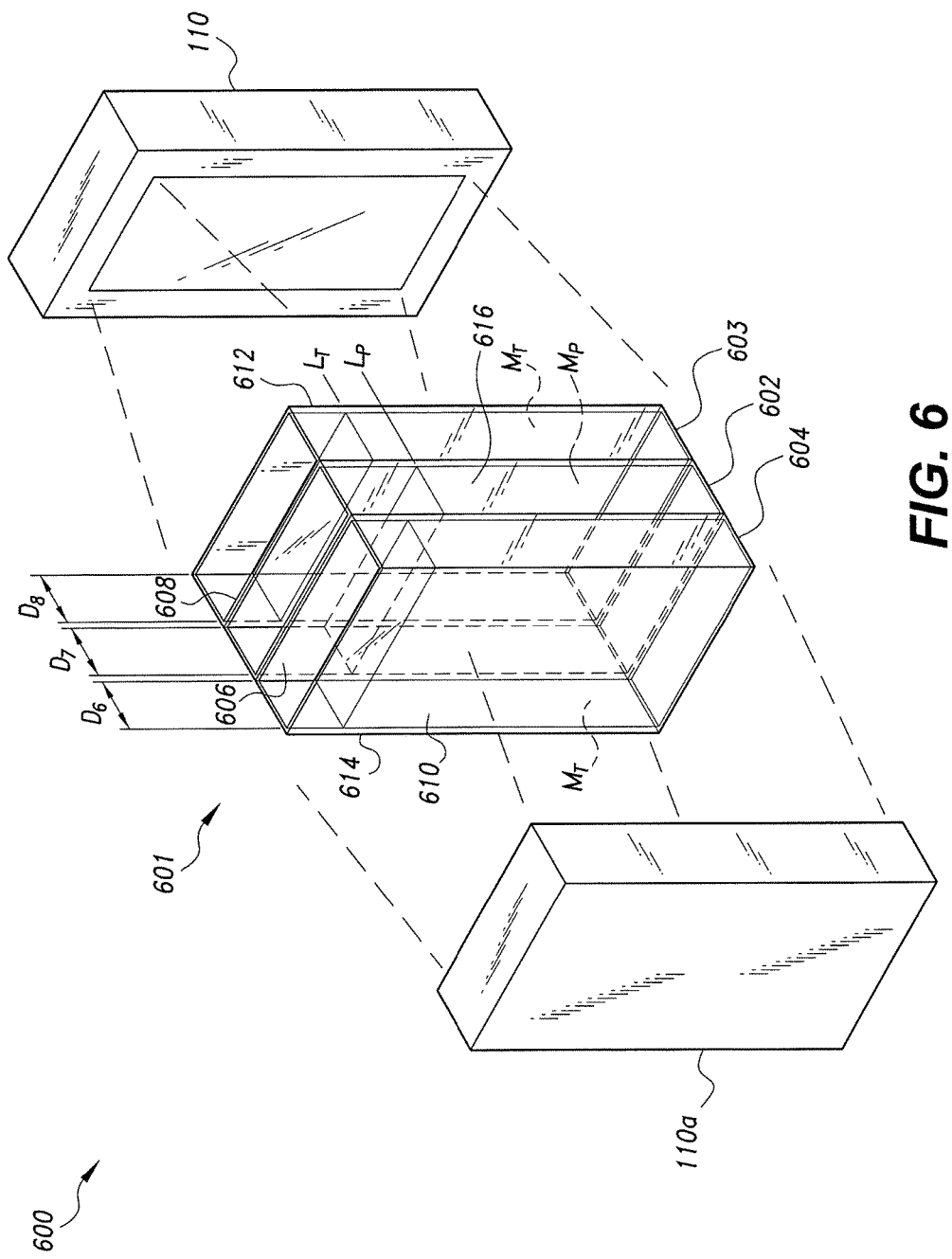
FIG. 6 is an environmental, perspective view of a fifth embodiment of an apparatus for testing the ability of materials to protect photolabile materials.

As shown in FIG. 6, a fifth embodiment of the apparatus 600 includes a unitary assembly 601, which has a first primary cell 604, a secondary cell 602 and a second primary cell 603 separated by transparent separating walls 606 and 608. The transparent separating wall 606 is a common wall between the secondary cell 602 and the first primary cell 604, while the transparent separating wall 608 is common between the secondary cell 602 and the second primary cell 603. The side wall 610 and the side wall 612 of the assembly 601 are transparent and allow transmission of light into the first primary cell 604 and the second primary cell 603, respectively. The rear wall 614 and the front wall 616 of the assembly 601 are opaque to block the transmission of light directly into the secondary cell 602, as well as to block the transmission of light into the secondary cell 602 through shortened paths through the primary cells 603 and 604. The walls are arranged generally orthogonal to one another, such that the front wall 616 and the rear wall 614 are parallel to one another and perpendicular to side walls 610 and 612 and separating walls 606 and 608. The bottom, the side walls and the separating walls are all planar and substantially rectangular, and are all orthogonal to each other.

The distance $D_7$ between separating walls 606 and 608 is preferably between 1.0 to 10.0 mm, more preferably 1.0 to 6.0 mm, and most preferably 2.0 to 3.0 mm. The distance $D_6$ between side wall 610 and separating wall 606 is preferably between 1.0 to 10.0 mm, more preferably 1.0 to 6.0 mm, and most preferably 2.0 to 3.0 mm. The distance $D_8$ between side wall 612 and separating wall 608 is preferably between 1.0 to 10.0 mm, more preferably 1.0 to 6.0 mm, and most preferably 2.0 to 3.0 mm. The photolabile material $M_P$ is placed inside the secondary cell 602, and the material under test $M_T$ is placed in the primary cells 603 and 604. The level $L_P$ of photolabile material $M_P$ inside the secondary cell 602 is maintained lower than the level $L_T$ of the material under test $M_T$, to avoid direct exposure of light on the photolabile material $M_P$. After filing the primary cells 603 and 604 and secondary cell 602, the open top of all three cells are closed with a suitable opaque closure (not shown). Once the materials have been placed in the cells, the assembly is illuminated using one or more light sources 110 and 110a. The light sources 110 and 110a can be placed at the top of the assembly 600 or to the side of assembly 600. The photolabile materials $M_P$ are withdrawn intermittently at predetermined time intervals and are analyzed to determine if any degradation of the photolabile materials $M_P$ has occurred.

Figure 7:
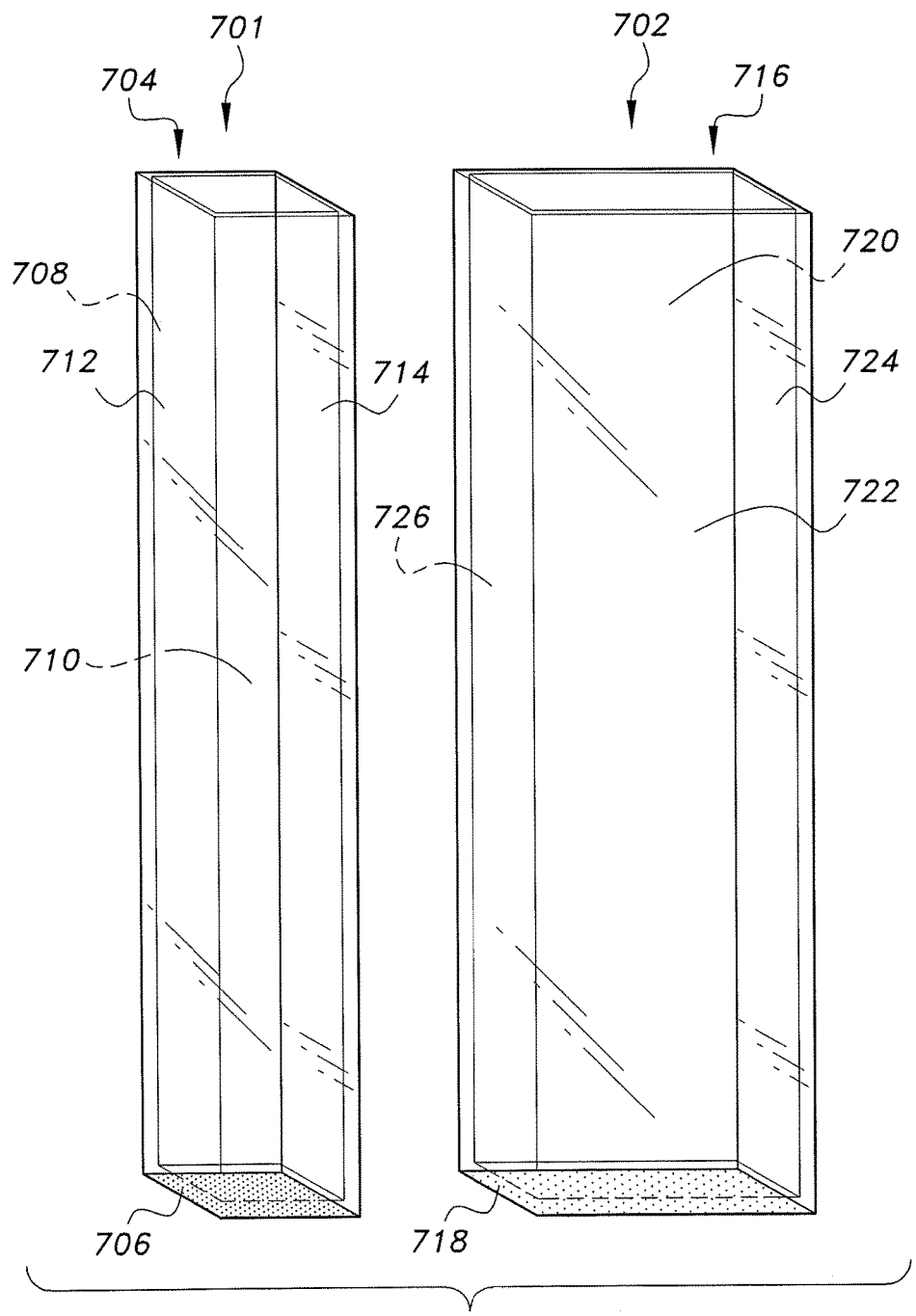
FIG. 7 is an environmental, perspective view of two cells for use in an apparatus for testing the ability of materials to protect photolabile materials.

In FIG. 7, two cells are shown, including a primary cell 701; and a secondary cell 702. The primary cell 701 has an open end 704 and a closed bottom 706. The primary cell 701 also has: a rear wall 708 and a front wall 710, which are opaque; and side walls 712 and 714, which are transparent. The secondary cell 702 has an open end 716 and a closed bottom 718. The secondary cell 702 also has a rear wall 720, a front wall 722, and a right-side wall 724, which are opaque, and a left-side wall 726, which is transparent. The bottom and the side walls of both the primary cell 701 and the secondary cell 702 are all planar and substantially rectangular, and are all orthogonal to each other. As is described further below, the primary cell 701 and secondary cell 702 are placed together in such a way that one of the transparent side walls 712 or 714 of the primary cell 701 is in intimate contact with the transparent wall 726 of the secondary cell 702.

Figure 8:
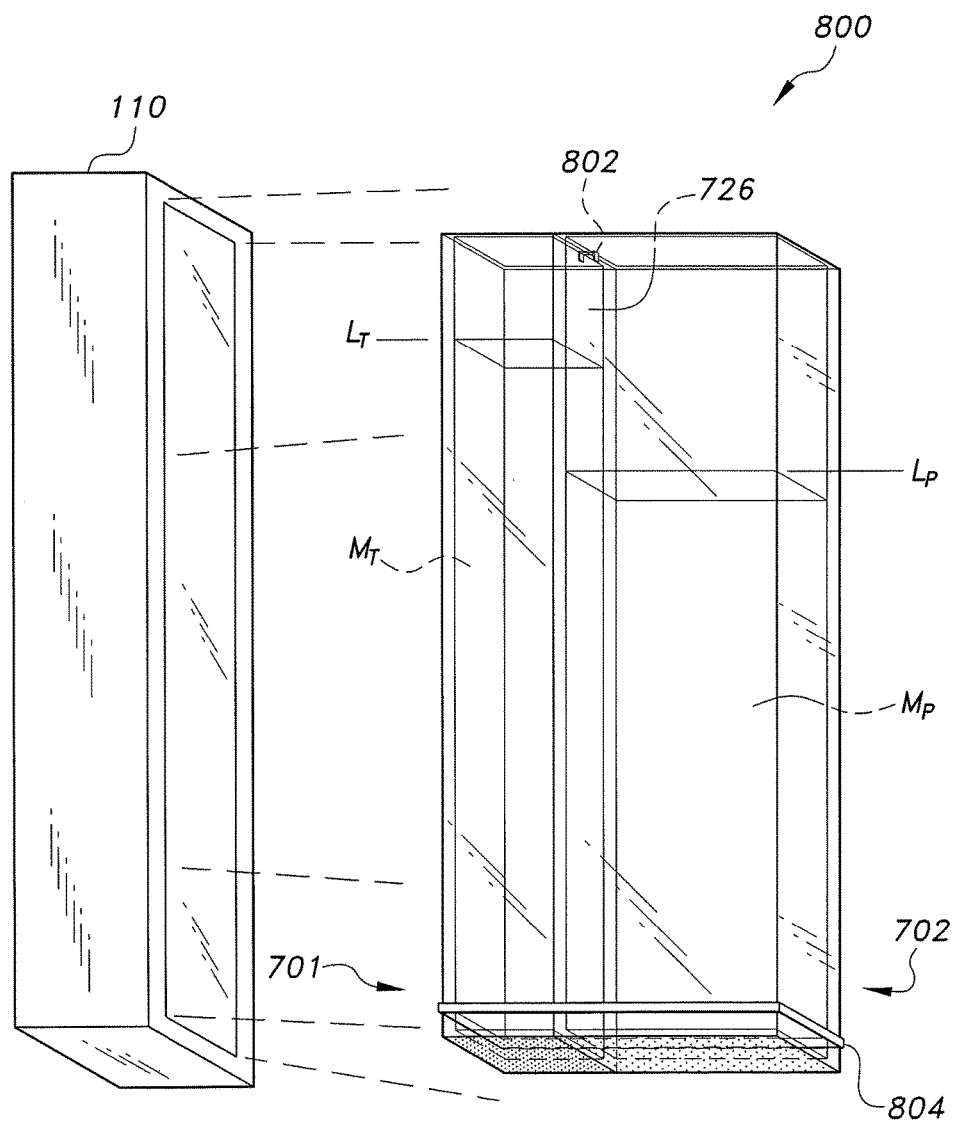
FIG. 8 is an environmental, perspective view of a sixth embodiment of an apparatus for testing the ability of materials to protect photolabile materials, using the cells shown in FIG. 7.

FIG. 8 shows a sixth embodiment 800 of an apparatus for testing the ability of materials to protect photolabile materials. The apparatus 800 includes one primary cell 701, one secondary cell 702, and a light source 110. The cells 701 and 702 are held together with a clip 802 and a band 804, such that the transparent side wall 714 of the primary cell 701 is adjacent to and aligned with the transparent left-side wall 726 of the secondary cell 702. The photolabile material $M_P$ is placed inside the secondary cell 702, and the material under test $M_T$ is placed in the primary cell 701. The level $L_P$ of photolabile material $M_P$ inside the secondary cell 702 is maintained lower than the level $L_T$ of the material under test $M_T$ inside the primary cell 701 to avoid direct exposure of light on the photolabile material $M_P$. After filling the primary cell 701 and secondary cell 702, the open ends of both the cells are closed with a suitable opaque closure (not shown). Once the materials have been placed in the cells, the assembly is illuminated using a light source 110. The light source 110 can be placed at the top of the assembly 800 or to the side of assembly 800. The photolabile material $M_P$ is withdrawn intermittently at predetermined time intervals and is analyzed to determine if any degradation of the photolabile material $M_P$ has occurred.

Figure 9:
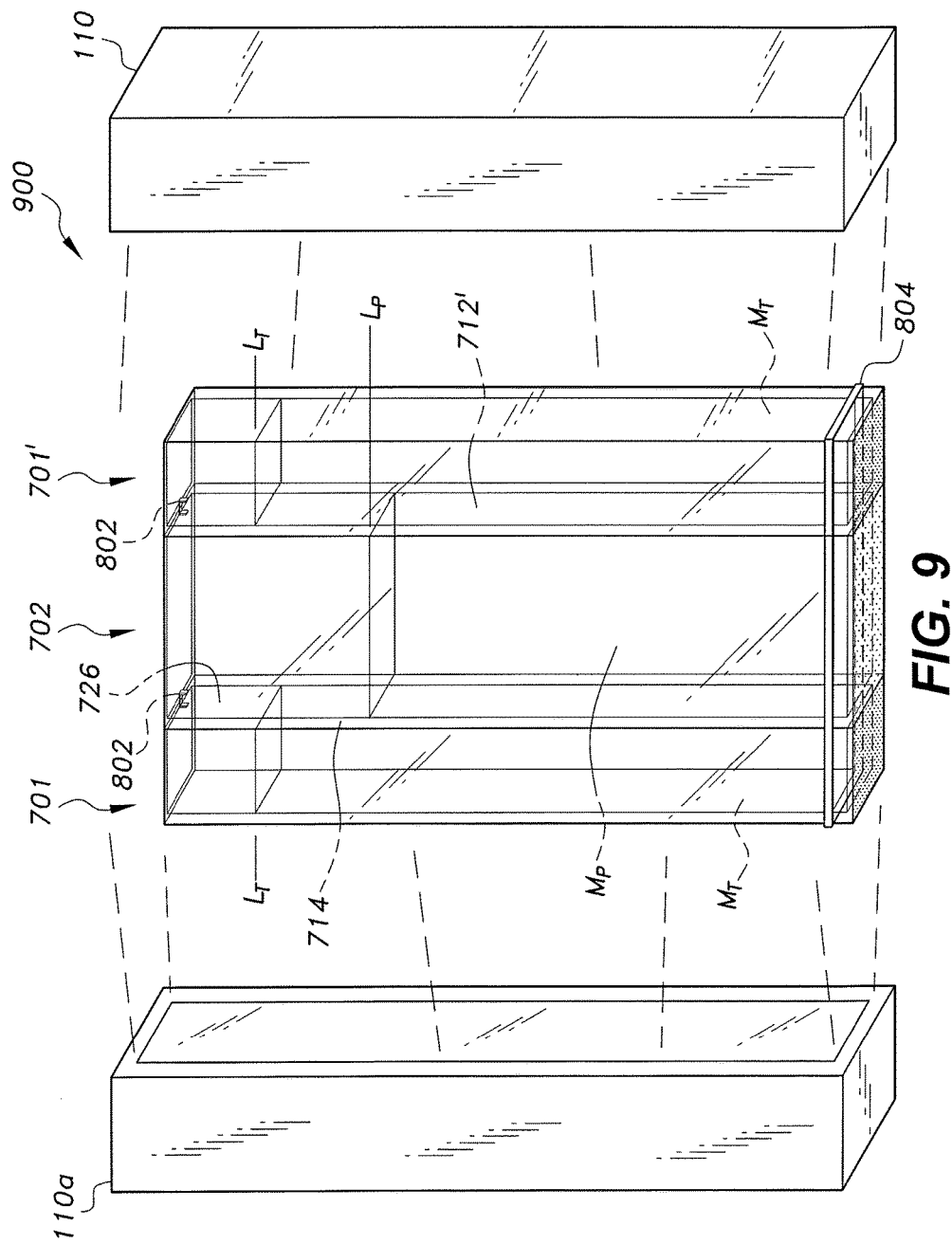
FIG. 9 is an environmental, perspective view of a seventh embodiment of an apparatus for testing the ability of materials to protect photolabile materials, using the components shown in FIG. 7.

FIG. 9 shows a seventh embodiment 900 of an apparatus for testing the ability of materials to protect photolabile materials. The apparatus 900 includes two primary cells 701 and 701', one secondary cell 702, and one or more light sources 110 and 110a. The secondary cell 702 is located between the first primary cell 701 and the second primary cell 701'. The cells 701, 701', and 702 are held together with two clips 802 and a band 804, such that the transparent side wall 714 of the primary cell 701, is adjacent to and aligned with the transparent left-side wall 726 of the secondary cell 702, and the transparent side wall 712' of the primary cell 701' is adjacent to and aligned with the transparent right-side wall 724 of the secondary cell 702. The photolabile material $M_P$ is placed inside the secondary cell 702, and the material under test $M_T$ is placed in the primary cells 701 and 701'. The material under test $M_T$ in the primary cell 701' may be the same as that in primary cell 701, or it may be a different material to allow testing two different materials simultaneously. The level $L_P$ of photolabile material $M_P$ inside the secondary cell 702 is maintained lower than the level $L_T$ of the material under test $M_T$ inside the primary cells 701 and 701' to avoid direct exposure of light onto the photolabile material $M_P$. After filling the primary cells 701 and 701' and the secondary cell 702, the open ends of all the cells are closed with a suitable opaque closure (not shown). Once the materials have been placed in the cells, the assembly is illuminated using one or more light sources 110 and 110a. The light sources 110 and 110A can be placed at the top of the assembly 900 or to the side of assembly 900. The photolabile material $M_P$ is withdrawn intermittently at predetermined time intervals and is analyzed to determine if any degradation of the photolabile material $M_P$ has occurred.

As noted above, in the seventh embodiment, a secondary cell 702 is sandwiched between two primary cells 701 and 701'. In a further embodiment, a secondary cell 702 having four transparent side walls is sandwiched between four primary cells 701. The two opposite side walls of the primary cells 701 are opaque and two side walls are transparent. The transparent walls of the primary cells allow the passage of light into the secondary cell. Four different materials can be tested simultaneously by filling each primary cell with a different material.

Figure 10A:
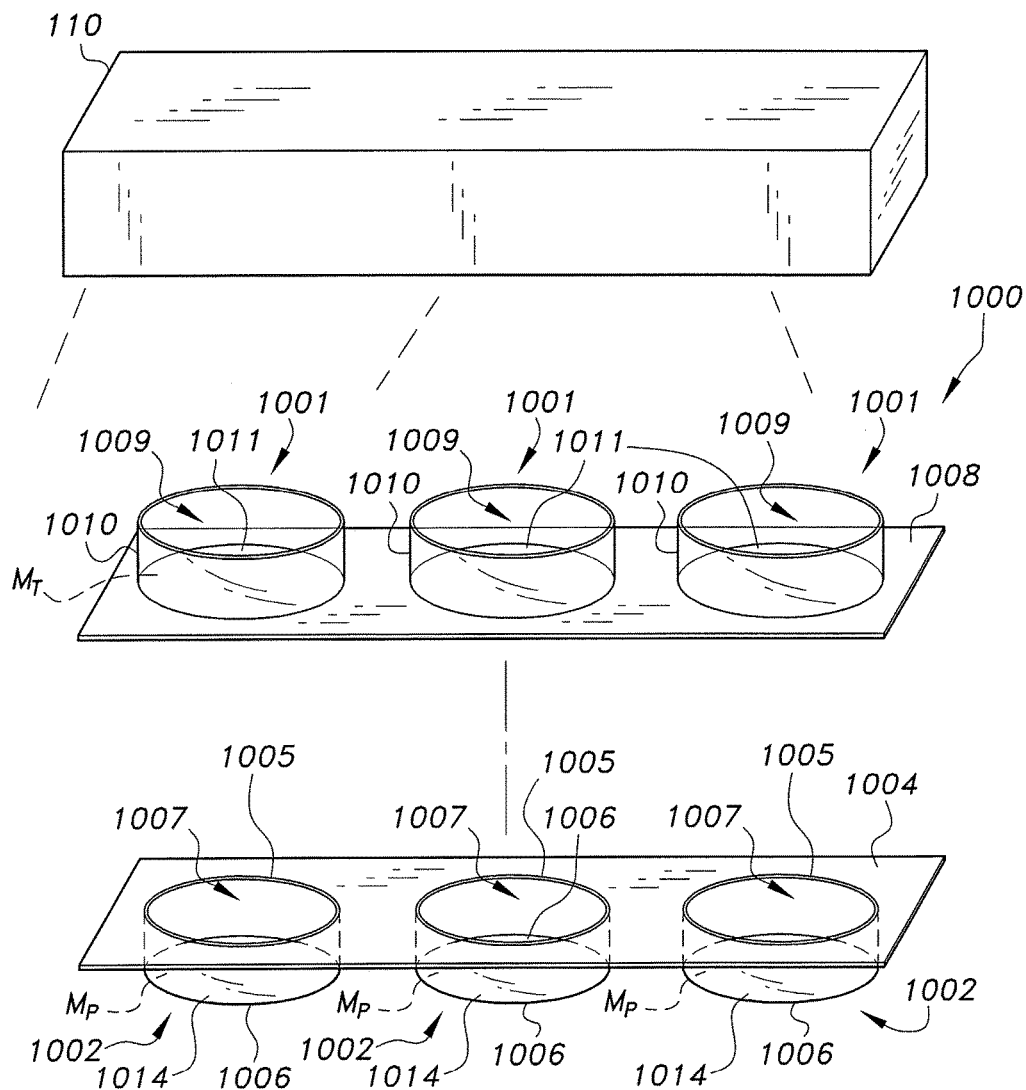
FIG. 10A is a perspective view of an eighth embodiment of an apparatus for testing the ability of materials to protect photolabile materials, shown with an assembly of primary cells exploded above an assembly of secondary cells.
Figure 10B:
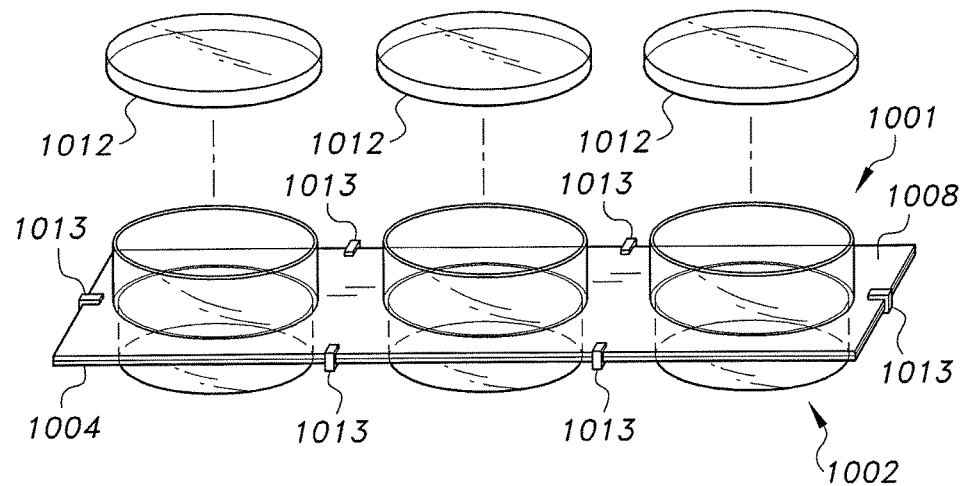
FIG. 10B is a perspective view of the apparatus of FIG. 10A, shown with the assembly of primary cells attached to the assembly of secondary cells.
Figure 11:
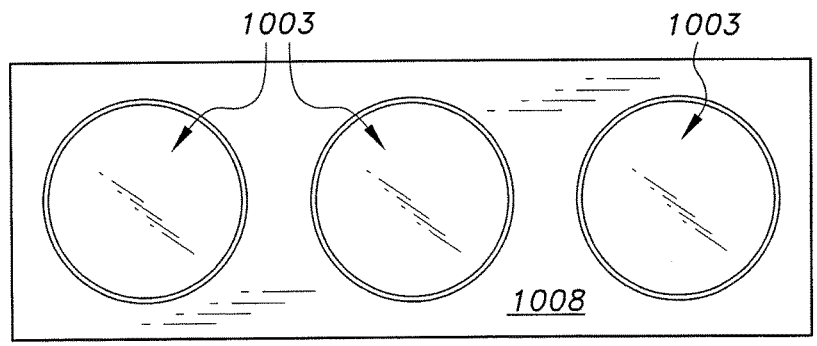
FIG. 11 is a top view of a flat sheet component supporting the primary cells of the apparatus of FIGS. 10A and 10B.

FIGS. 10A, 10B and 11 show an eighth embodiment of an apparatus 1000 for testing the ability of materials to protect photolabile materials. The apparatus 1000 includes numerous primary cells 1001 and an equivalent number of secondary cells 1002. Each primary cell 1001 has an open end 1009, transparent or opaque side walls 1010, and a transparent bottom 1011. Each primary cell is fixed in a suitable opening 1003 of an opaque flat sheet 1008 (see FIG. 11). The material under testing $M_T$ is filled in the primary cells 1001. Each secondary cell 1002 comprises opaque peripheral walls 1014 and an opaque bottom 1006, and an open top 1007. The secondary cells 1002 are fixed on a flat sheet 1004, in a manner similar to the blisters in tablet or capsule packaging strips. The photolabile material $M_P$ is placed inside the secondary cell 1002, up to the brim 1005. Different materials under test $M_T$ and different photolabile material $M_P$ can be filled in the different primary and secondary cells at the same time, such that multiple materials can be tested in different cells simultaneously. The filing depth of each primary cell 1001 as well as secondary cell 1002 is between 1 to 10 mm, more preferably 2 to 5 mm, most preferably 2 to 3 mm.

After filling the primary cells 1001 and secondary cells 1002, the primary cells are closed by using a suitable transparent cap 1012, and then whole sheet 1008 containing filled primary cells is placed over the sheet 1004 in such a way that the transparent bottoms 1011 of the primary cells 1001 act as lids over the top open ends 1007 of the secondary cells 1002. The sheets 1008 and 1004 are tightly connected using multiple clips 1013 at different locations. Once the cells are filled and fixed properly, the assembly is illuminated by the light source 110 at top of the apparatus 1000. The photolabile material $M_P$ is withdrawn intermittently at predetermined time intervals and is analyzed to determine if any degradation of the photolabile material $M_P$ has occurred.

Figure 12:
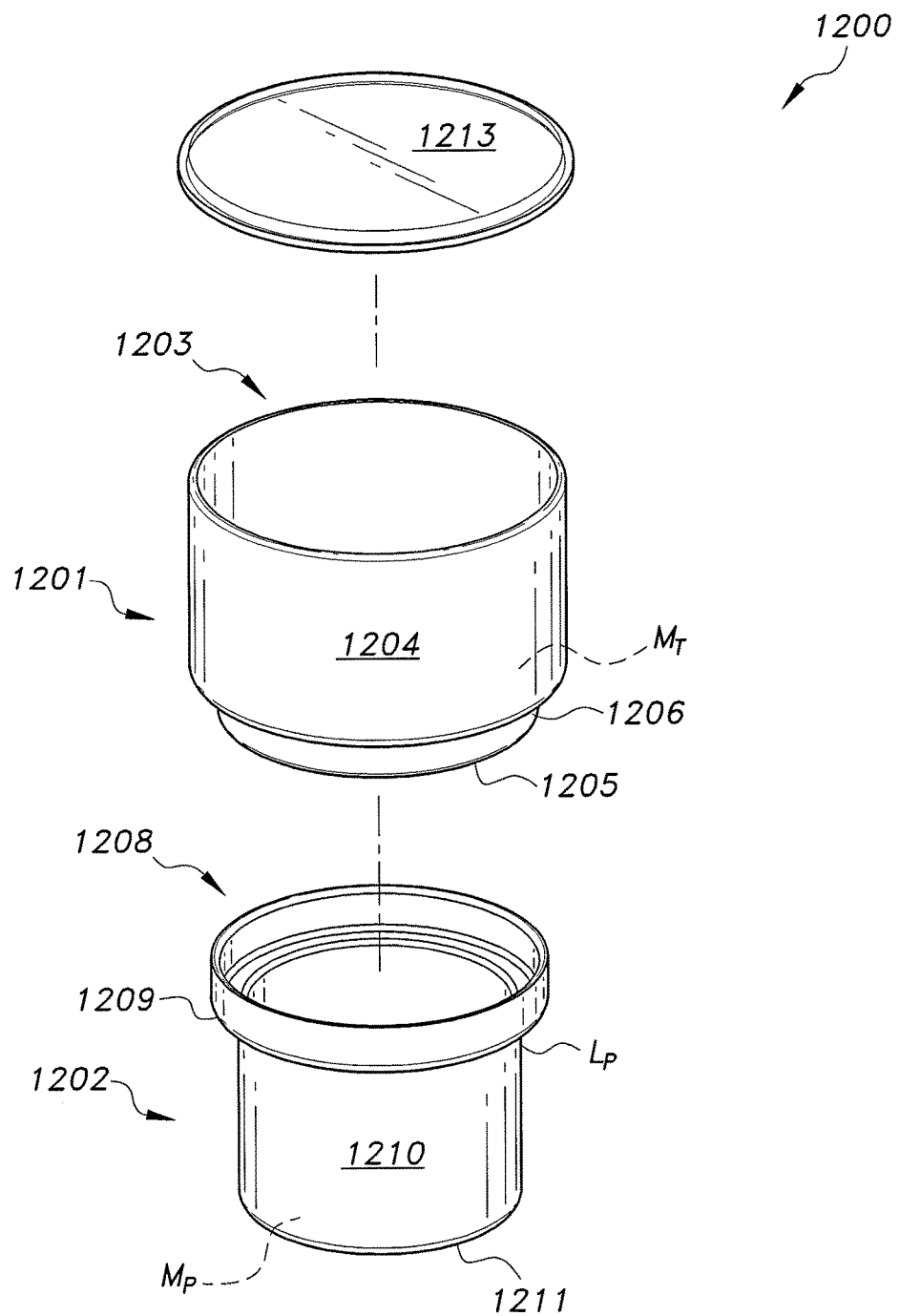
FIG. 12 is an exploded perspective view of a ninth embodiment of an apparatus for testing the ability of materials to protect photolabile materials.
Figure 13:
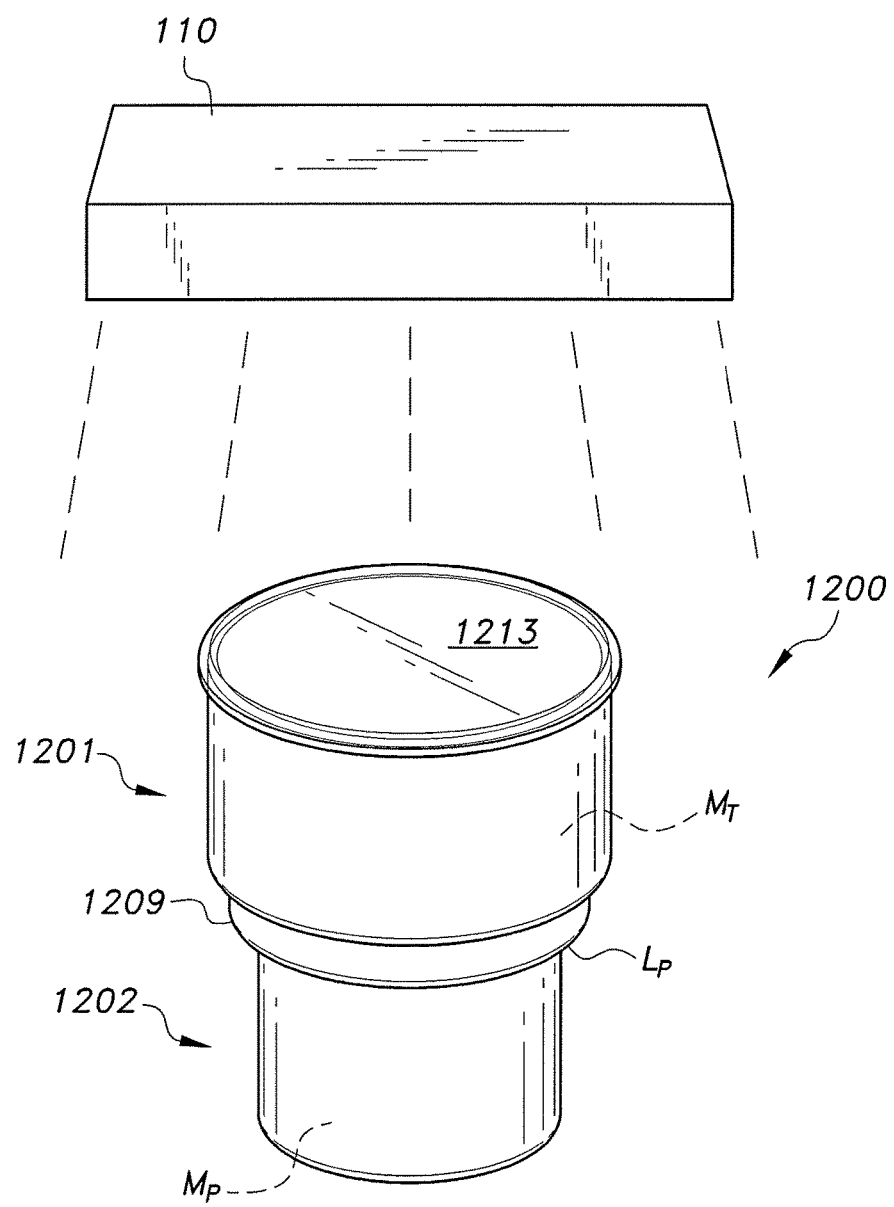
FIG. 13 is a perspective view of the apparatus of FIG. 12 following assembly of the primary cell to the secondary cell.

FIGS. 12 and 13 show a ninth embodiment of an apparatus 1200 for testing the ability of materials to protect photolabile materials. The apparatus 1200 includes one primary cell 1201, one secondary cell 1202, and a light source 110. The cells 1201 and 1202 are held together in vertical position such that the transparent bottom 1205 of the primary cell 1201 is tightly held in the open wide mouth portion 1208 of the secondary cell 1202. The primary cell 1201 has an open end 1203, transparent or opaque side walls 1204, and a transparent bottom 1205. There is a small tapering 1206 at the junction of side walls 1204 and the transparent bottom 1205 of the primary cell 1201. The open wide end 1208 of secondary cell 1202 also has a tapered section of the walls 1210 of secondary cell 1202 at an annular lip 1209. The walls 1210 and the bottom 1211 of the secondary cell 1202 are opaque and do not allow passage of light. The photolabile material $M_P$ is placed inside the secondary cell 1202, and the material under test $M_T$ is placed in the primary cell 1201. The filling depth of the primary cell 1201 and the secondary cell 1202 is between 1 to 10 mm, more preferably 2 to 5 mm, and most preferably 2 to 3 mm. The level $L_p$ of photolabile material $M_P$ inside the secondary cell 1202 is maintained near the lip 1209. The material under test $M_T$ is placed inside the primary cell 1201. After filling the primary cell 1201 and secondary cell 1202, the open end of the primary cell 1201 is closed with a suitable transparent cap 1213, and then primary cell 1201 is placed over the secondary cell 1202 in such a manner that the transparent bottom 1205 of primary cell 1201 fits perfectly inside the open wide mouth part 1208 of the secondary cell 1202. Once the filled cells are arranged in a suitable manner, as presented in FIG. 13, the apparatus 1200 is illuminated using a light source 110. The photolabile material $M_P$ is withdrawn intermittently at predetermined time intervals and is analyzed to determine if any degradation of the photolabile material $M_P$ has occurred.

It is to be understood that the apparatus and method for testing the ability of materials to protect photolabile materials is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:
1. An apparatus for testing the ability of materials to protect photolabile materials, comprising:

at least one primary cell;
at least one secondary cell, wherein the at least one secondary cell is disposed within and is surrounded by the at least one primary cell whereby a gap is provided between the cells, further wherein the at least one secondary cell is substantially of equal height with the at least one primary cell;
a material under test substantially filling the gap between the at least one primary cell and the at least one secondary cell and being at a first level therewithin;
a photolabile material disposed within the at least one secondary cell and being at a lower level than the first level of the material under test; and
a light source for emitting light, wherein the at least one primary cell and the at least one secondary cell being positioned so that substantially all light emitted by the light source entering the at least one secondary cell traverses the at least one primary cell.

2. The apparatus according to claim 1, wherein the at least one primary cell and the at least one secondary cell are a unitary assembly, the assembly having a bottom, four side walls and at least one separating wall.

3. The apparatus according to claim 2, wherein the bottom, the four side walls and the separating wall are planar and substantially rectangular, and are all orthogonal to each other.

4. The apparatus according to claim 2, wherein:
the at least one primary cell consists of a single primary cell;
the at least one secondary cell consists of a single secondary cell; and
the at least one separating wall consists of a single separating wall.

5. The apparatus according to claim 2, wherein:
the at least one primary cell comprises two primary cells;
the at least one secondary cell comprises a single secondary cell; and
the at least one separating wall comprises two separating walls.

6. The apparatus according to claim 1, wherein the at least one primary cell and the at least one secondary cell are two separate components, each of the components having a closed bottom and four side walls, the closed bottom and the four side walls all being planar and substantially rectangular, and all being orthogonal to each other.

7. The apparatus according to claim 6, wherein:
the at least one primary cell consists of a single primary cell;
the at least one secondary cell consists of a single secondary cell; and
the apparatus further comprises a single clip and a band for holding the single primary cell and the single secondary cell together.

8. The apparatus according to claim 6, wherein:
the at least one primary cell comprises two primary cells;
the at least one secondary cell consists of a single secondary cell; and
the apparatus further comprises two clips and a band for holding the two primary cells and the single secondary cell together.

9. The apparatus according to claim 1, wherein the emitted light cannot exit the at least one secondary cell without further traversing the at least one primary cell.

10. The apparatus according to claim 1, wherein the at least one primary cell consists of a single primary cell.

11. The apparatus according to claim 10, wherein the at least one secondary cell consists of a single secondary cell.

12. The apparatus according to claim 11, wherein:
the single primary cell is a first cylindrical tube closed at one end and open at the other end;
the single secondary cell is a second cylindrical tube closed at one end and open at the other end.

13. The apparatus according to claim 12, wherein the single secondary cell includes projections on an outer surface of a side wall of the single secondary cell maintaining the single secondary cell centrally aligned within the single primary cell and maintaining an equal gap on all sides between an inner wall of the single primary cell and the outer surface of the single secondary cell, defining a sample chamber between the primary cell and the secondary cell.

14. The apparatus according to claim 12, further comprising a cap having a body, a central projection and a peripheral wall, the central projection fitting inside the open end of the single secondary cell and the peripheral wall covering an outer wall of the single primary cell near the open end of the single primary cell.

15. The apparatus according to claim 11, wherein:
the single primary cell comprises a planar, substantially square bottom and four planar, substantially rectangular side walls orthogonal to each other; and
the single secondary cell comprises a planar, substantially square bottom and four planar, substantially rectangular side walls orthogonal to each other.

16. The apparatus according to claim 15, further comprising a cap having a body, a central projection and a peripheral wall, the central projection fitting inside the open end of the single secondary cell and the peripheral wall covering an outer wall of the single primary cell near the open end of the single primary cell.

17. An apparatus for testing the ability of materials to protect photolabile materials, comprising:
at least one primary cell, wherein the at least one primary cell comprises a transparent, planar, substantially rectangular bottom and four planar, substantially rectangular side walls orthogonal to the bottom and to each other;
a plurality of secondary cells, wherein each of the plurality of secondary cells comprises a transparent cylindrical capillary having opposed open ends;
plugs closing each of the opposed open ends of the plurality of secondary cells; and
a light source for emitting light, the primary cell, and the secondary cells being positioned so that substantially all light emitted by the light source entering the secondary cells traverses the at least one primary cell.

18. The apparatus according to claim 17, further comprising:
a plurality of straight thin wires; and
a plurality of small circular rings of thin wire, each of the small circular rings surrounding one of the secondary cells and each of the straight thin wires extending between one of the plurality of small circular rings of thin wire and inner side walls of the primary cell, thereby keeping the plurality of secondary cells in an upright and spaced position within the primary cell.

19. A method for testing the ability of a protective material to protect a photolabile material, the method comprising the steps of:
providing at least one primary cell;
providing at least one secondary cell, wherein the at least one primary cell surrounds the at least one secondary cell;
placing protective material in the at least one primary cell;

placing photolabile material in the at least one secondary cell;

subjecting the primary and secondary cells to a light source for a predetermined amount of time; and removing and testing the photolabile material for degradation to determine the ability of the protective material to protect the photolabile material.

\* \* \* \* \*